United States Patent [19]
Burton

[11] Patent Number: 5,960,471
[45] Date of Patent: Oct. 5, 1999

[54] PROTECTIVE GARMENT FOR USE WITH FEEDING, BURPING, NURSING AND CHANGING DIAPERS OF A BABY

[76] Inventor: Teresa Cheryl Burton, 2721 Temperance Dr., Myrtle Beach, S.C. 29577

[21] Appl. No.: 09/033,532

[22] Filed: Mar. 2, 1998

[51] Int. Cl.⁶ .............................. A41B 13/10; A41D 1/20
[52] U.S. Cl. ............................ 2/48; 2/104; 2/49.2; 2/49.4
[58] Field of Search ................................ 2/104, 49.1, 48, 2/49.2, 49.4, 50, 46, 47, 94; 362/103

[56] References Cited

U.S. PATENT DOCUMENTS

| | | |
|---|---|---|
| D. 155,752 | 10/1949 | Vivaudou . |
| 4,106,122 | 8/1978 | Dodd . |
| 4,563,777 | 1/1986 | Park . |
| 4,564,957 | 1/1986 | Scharf . |
| 4,710,979 | 12/1987 | Bull et al. . |
| 4,713,842 | 12/1987 | Patterson . |
| 5,182,813 | 2/1993 | Booze . |
| 5,312,282 | 5/1994 | Cooper . |
| 5,483,701 | 1/1996 | Ferreyros . |
| 5,490,289 | 2/1996 | Lehrer . |
| 5,509,141 | 4/1996 | Saltzman . |
| 5,570,945 | 11/1996 | Chien et al. . |
| 5,592,689 | 1/1997 | Matthews . |
| 5,799,336 | 9/1998 | Cooper . |

Primary Examiner—John J. Calvert
Assistant Examiner—Shirra L. Jenkins
Attorney, Agent, or Firm—Thomas L. Moses

[57] ABSTRACT

A protective garment for feeding, burping, nursing, and changing diapers of a baby, the garment having a main body member that may be secured about the neck and over the shoulders of a wearer, comprising an inner layer made from a waterproof material, such as vinyl, and an outer absorbent layer attached preferably on either side of the inner layer. The outer layer is made from soft material, such as cotton, fleece, flannel, or the like, which is suitable for soft contact with a baby's skin. A cloth member is removably attached to the front outer portion of the outer layer, and is used as a washcloth or napkin to clean a baby during or after feeding or burping. In the preferred embodiment, the front outer layer of the main body member includes a pair of pockets, having an elastic band about the top of the pockets for retaining baby bottles or other baby care items. The back outer layer contains a plurality of pockets on a bottom portion, and also includes a small pocket adjacent the neck area for containing a small musical device. Other features described herein include a lap pad, removably secured on the back outer layer, which can be folded down over the wearer's lap for changing diapers, glow in the dark designs on the front outer layer, VELCRO loops for holding teething rings, pacifiers, baby keys, and the like, and openings provided adjacent a female wearer's breasts for providing access for a baby to the breast for nursing.

12 Claims, 3 Drawing Sheets

PROTECTIVE GARMENT FOR USE WITH FEEDING, BURPING, NURSING AND CHANGING DIAPERS OF A BABY

BACKGROUND OF THE INVENTION

1. Field of the Invention

The present invention relates generally to protective garments used by parents or care givers for feeding, nursing, burping, or changing diapers of babies. In the course of taking care of a baby, it is difficult to feed or burp the baby while protecting the clothing of the care giver. It would, therefore, be desirable to provide a garment that could be easily slipped on over a care giver's clothing to protect against food spillage and regurgitation that is associated with baby care. Further, it would be desirable to provide a protective garment that has a lap pad, which can be secured in a closed position when not in use, and which can be opened to cover the lap of a care giver for changing diapers, particularly in a situation where there is no diaper changing station nearby.

Specifically, the present invention includes a protective garment having a main body member that may be secured about the neck and over the shoulders of a wearer, comprising an inner layer made from a waterproof material, such as vinyl, and an outer absorbent layer attached preferably on either side of the inner layer. The outer layer is made from soft material, such as cotton, fleece, flannel, or the like, which is suitable for soft contact with a baby's skin. A cloth member is removably attached to the front outer portion of the outer layer, and is used as a washcloth or napkin to clean a baby during or after feeding or burping. The means for attaching the cloth member may be snaps, hook and loop fasteners, such as VELCRO, or any other suitable means for removable securement.

In the preferred embodiment, the front outer layer of the main body member includes a pair of pockets, having an elastic band about the top of the pockets for retaining baby bottles or other baby care items. The back outer layer, which is the layer adjacent the clothing of the wearer, contains a plurality of pockets on a bottom portion, and also includes a small pocket adjacent the neck area for containing a small musical device. The musical device may be activated or deactivated by simply depressing a button located on the device. Other features described herein include a lap pad, removably secured on the back outer layer, which can be folded down over the wearer's lap for changing diapers, glow in the dark designs on the front outer layer, VELCRO loops for holding teething rings, pacifiers, baby keys, and the like, and slits provided adjacent a female wearer's breasts for providing access for a baby to the breast for nursing.

2. Discussion of the Prior Art

Quilling, et al. U.S. Pat. No. 4,660,226

Bull, et al. U.S. Pat. No. 4,710,979

Trombetti-Dickens U.S. Pat. No. 4,924,528

Deon U.S. Pat. No. D381,190

The Quilling reference discloses a bib having a rectangular pad, and having a first absorbent layer and a second waterproof layer with adhesive strips provided for securement thereto. The bib has a pocket at the bottom of the bib, and extensions to allow the bib to be closely fitted around the neck of a wearer.

The Bull patent teaches a mother's apron or bib with detachable multicolored two-dimensional toys to aid supervised baby play. The bib includes detachable letters, a detachable Noah's ark toy, a butterfly having a zipper revealing a mirror, and other features designed to teach baby manipulation skills.

The Trombetti-Dickens reference shows a bib garment for covering a mother's nursing baby, wherein the bib incorporates a primary panel having its upper edge shaped to fit the neck of the nursing mother. The panel is described as being wide enough to cover the front and sides of the mother and her baby while nursing, and the bib contains pockets near the lower edge on the inside face of the bib for storage and access to nursing necessities and equipment.

The Deon patent is a design patent showing a newborn baby apron having various pockets and features for storing a variety of baby care items.

None of the prior art, however, discloses a machine washable protective garment having an inner waterproof layer and an outer soft absorbent layer, together with a removable cloth, pockets on the front side and the back side, where the garment fits about the neck and over the shoulders and arms to protect the wearer's clothing during nursing, feeding, and changing diapers. Further, none of the prior art discloses a protective garment having a lap pad removably positioned on the back side of the garment, which may be released at a point adjacent the neck area and folded down over the wearer's lap for changing diapers, and which can be resecured about the neck area after use.

SUMMARY OF THE INVENTION

Accordingly, it is an important object of the present invention to provide a machine washable protective garment for a baby care giver to prevent the clothing of the care giver from becoming soiled during feeding, nursing, burping or changing the diapers of a baby.

Another important object of the present invention is to provide a protective garment for baby care givers, where the garment contains a plurality of pockets for storage and accessibility to various baby care items and equipment.

Yet another important object of the present invention is to provide a protective garment for baby care givers, where the garment includes a detachable lap pad removably secured on the back portion of the garment adjacent the wearer's clothing, which may be released from the neck area and folded down over the lap of the wearer for changing the diapers of a baby.

A further object of the present invention is to provide a protective baby care garment having a musical device disposed thereon for entertaining and soothing a baby.

Yet another important object of the present invention is to provide a protective baby care garment having glow in the dark designs, animals, cartoon characters, or the like, which is pleasing to a baby, and which allows a wearer to find the garment during the night without disturbing the baby by turning on a light.

Another important object of the present invention is to provide a baby care protective garment having a removable cloth positioned on a front portion of the garment that may be used for cleaning a baby before, during or after feeding, nursing or burping.

Yet another important object of the invention is to provide a protective baby care garment that includes VELCRO loops for retaining teething rings, pacifiers, baby keys, or the like.

Another important object of the invention is to provide a protective baby care garment that contains slits adjacent a female wearer's breasts to provide access for a baby to the mother's breast for nursing.

A further important object of the present invention is to provide a protective baby care garment that is inexpensive to manufacture and overcomes some of the shortcomings of previous baby care aprons and bibs.

These and other features, aspects, and advantages of the present invention will become better understood with regard to the following description, appended claims, and accompanying drawings.

BRIEF DESCRIPTION OF THE DRAWINGS

The construction designed to carry out the invention will be hereinafter described, together with other features thereof.

The invention will be more readily understood from a reading of the following specification and by reference to the accompanying drawings forming a part thereof, wherein an example of the invention is shown and wherein.

DESCRIPTION OF THE PREFERRED EMBODIMENT

Figure 1:
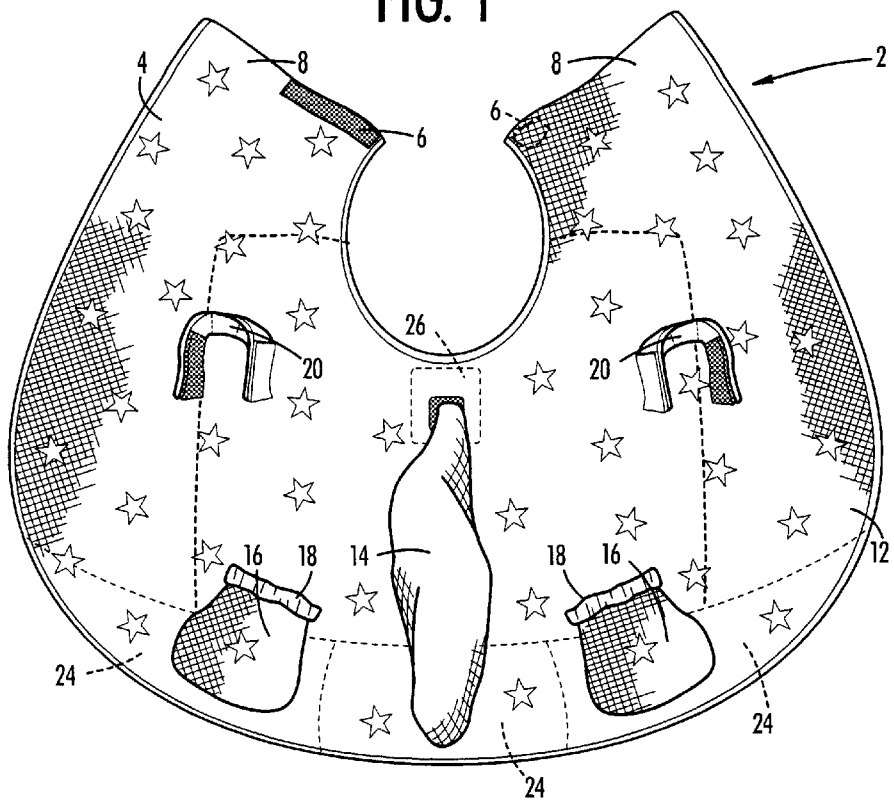
FIG. 1 is a perspective view of the front side of the baby care protective garment, and showing the features described herein.

As shown in FIG. 1, the baby care protective garment 2 comprises a main body member 4 that fits around the neck of a wearer, so that the protective garment covers the upper torso area of the wearer's clothing, including the shoulder and upper back areas. Fastening means 6 are positioned on the upper flaps 8 of the main body member for securement about the neck. These fastening means may be in the form of snaps, VELCRO, or any other suitable means providing quick and easy fastening and unfastening of the flaps.

Figure 4:
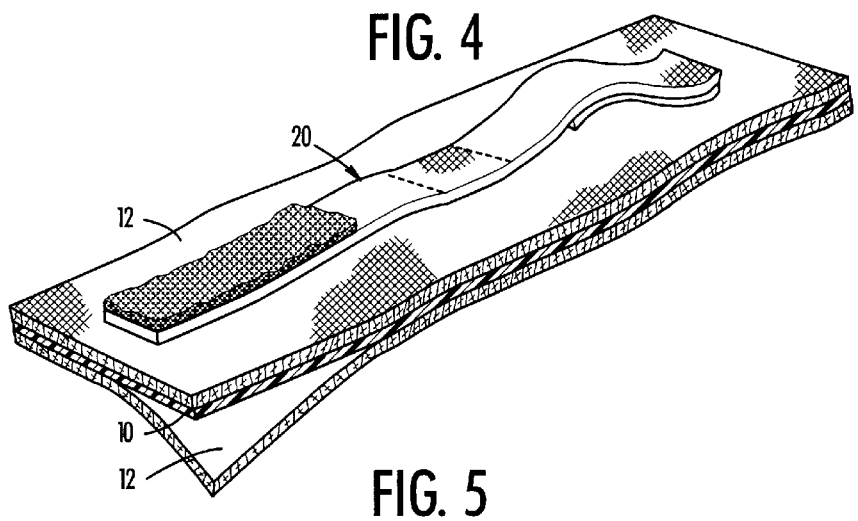
FIG. 4 is a cut away view of the front of the baby care protective garment showing the outer absorbent layers and the inner waterproof layer, and also showing the VELCRO loop attached to the front outer layer of the garment.

The main body member includes an inner waterproof layer 10, shown in FIG. 4, preferably vinyl or thick plastic, covered on both the front side (shown in FIG. 1) and on the back side (shown in FIG. 2) with an outer absorbent layer 12, preferably made of cotton, fleece, flannel, or any other soft absorbent material suitable for contact with a baby's skin. A cloth member 14 is removably attached, preferably with snaps or VELCRO, to the front portion of the main body member for use in cleaning the baby's skin before, during, or after feeding, nursing or burping the baby. The main body member also includes front pockets 16 having an elastic or otherwise stretchable portion 18 across the top of the pockets for holding a baby bottle or other baby equipment.

The front side of the outer layer may also include ornamental designs or drawings of animals, cartoon characters, and any other suitable visual material. In a preferred embodiment, glow in the dark material is used for at least part of the ornamental design, providing a pleasing effect for the baby and allowing the user to locate the protective garment at night without having to disturb the baby by turning on a light. VELCRO loops 20 are provided on the front side of the outer layer for removably retaining teething rings, pacifiers, baby keys, or the like. A pair of slits 22 are provided adjacent a female wearer's breasts, allowing the baby access to the mother's breast for nursing. The slits may be provided with means for securing the slits in a closed position, preferably by means of VELCRO strips or snaps.

Figure 2:
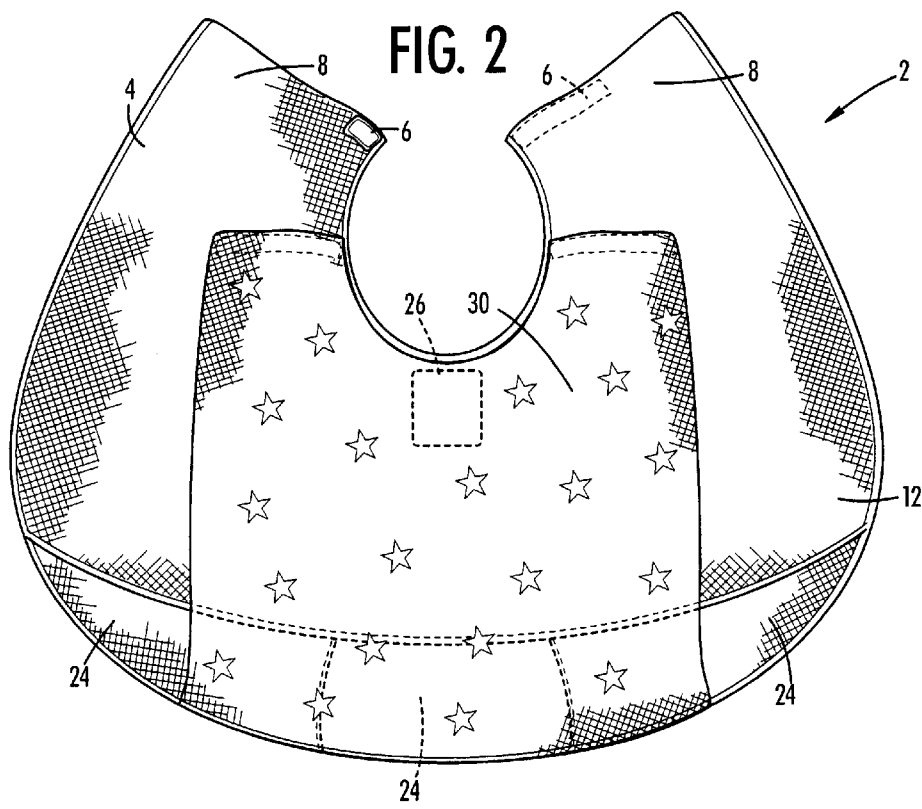
FIG. 2 is a perspective view of the back side of the baby care protective garment, further showing the lap pad in its closed position when not in use.

FIG. 2 illustrates the back side of the protective garment. A plurality of pockets 24 are disposed along the bottom portion of the back side of the protective garment for holding such items as diapers, small trash bags for soiled diapers, baby powder, wet wipes, and the like. Another small pocket 26 is positioned adjacent the neck area of the garment for holding a small musical device (not shown), which may be activated or deactivated by pressing a button positioned on the musical device. A lap pad 30 is removably secured to the back side of the garment, preferably by means of snaps or VELCRO strips. The fastening means for the lap pad are located adjacent the neck area of the garment, as well as at the bottom portion of the garment adjacent the bottom of the pockets 24. This arrangement allows for a wearer to simply unfasten the fastening means of the lap pad adjacent the neck area, while leaving the lower portion of the lap pad attached to the garment. The user then pulls the lap pad downwardly from the closed position and drapes the lap pad over the lap, for changing the baby's diapers. When the diaper changing is complete, the wearer may then refasten the lap pad into the original closed position about the neck, or if the lap pad is soiled, it may be completely removed from the garment and placed into a small trash bag and stored for later washing.

Figure 3:
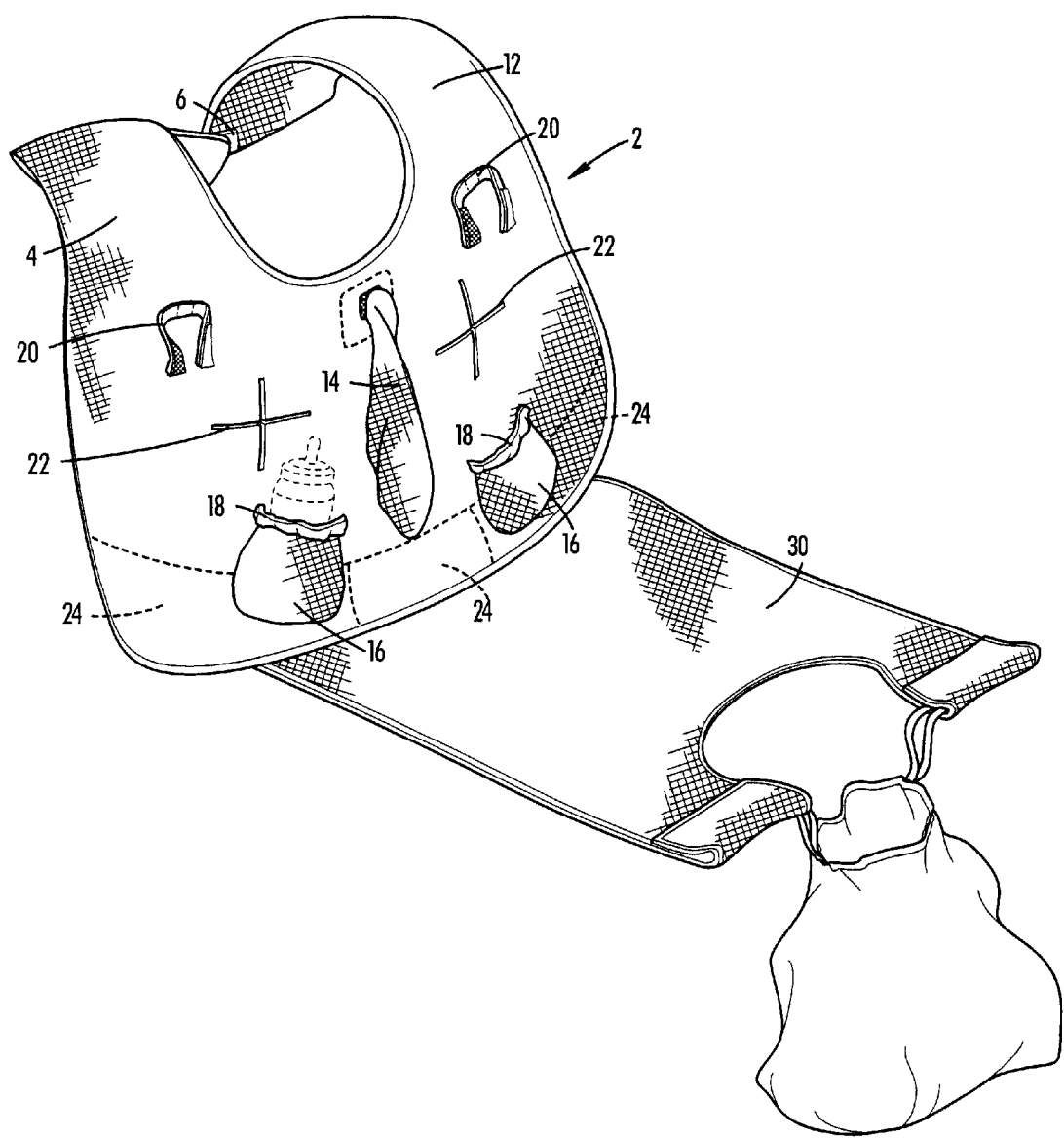
FIG. 3 is a perspective view of the front side of the baby care protective garment, illustrating the lap pad in its open position for use when a wearer is changing a baby's diaper.

FIG. 3 shows the lap pad in the open position, where the top portion of the lap pad has been released from the garment and the bottom portion of the lap pad is still affixed to the bottom of the garment. The fasteners located on the free end of the lap pad in this position may also be used to hold an open trash bag by simply securing the fasteners in a loop configuration about the handles of the trash bag.

FIG. 4 shows a cut-away view of a portion of the protective garment, showing the VELCRO loop attached to the outer front layer of the garment. The inner layer is illustrated as being sandwiched between the two outer layers, and the back outer layer is shown on the underside of the inner layer.

The protective baby garment is machine washable and capable of being dried in a conventional clothing dryer. The musical device should be removed before washing and drying, and replaced after the drying cycle has been completed, to avoid damage to the musical device. The absorbent outer layer of the garment provides a soft and slightly cushioned surface for supporting the baby's body and head. The garment may also be used in an automobile by hanging the garment from the clothing hook adjacent a window to shield a baby from direct sunlight, similarly to the suction cup shades commonly used for the same purpose.

In an alternate embodiment, the upper flaps of the main body member may also include open pockets that are positioned to catch regurgitated material that a baby spits up over the shoulder of the wearer. In this embodiment, when the person is wearing the protective garment, the pockets are located directly below the shoulders in the back of the garment. This arrangement reduces the likelihood that the regurgitated material will drip down the back of the garment and onto the clothing of the wearer.

Other different embodiments of the present apparatus include a male version of the protective garment wherein the attached cloth member resembles a man's tie, and the neck area is fitted with a type of collar to resemble a collared shirt. Also, the musical device may correspond with the ornamental design of the garment. For instance, the ornamental design may contain a night sky scene with glow in the dark stars and other heavenly bodies, and the musical device may play the tune of "Twinkle, Twinkle Little Star." Other corresponding themes may include Christmas or other holidays, or any other theme combination between the music and the ornamental design.

The protective garment may, in another alternate embodiment, be made from disposable material, so that the wearer may wear the garment until it becomes soiled, and then simply dispose of the garment. In the disposable embodiment, the garment may be made from a single layer of plastic, or any other suitable waterproof material.

Figure 5:
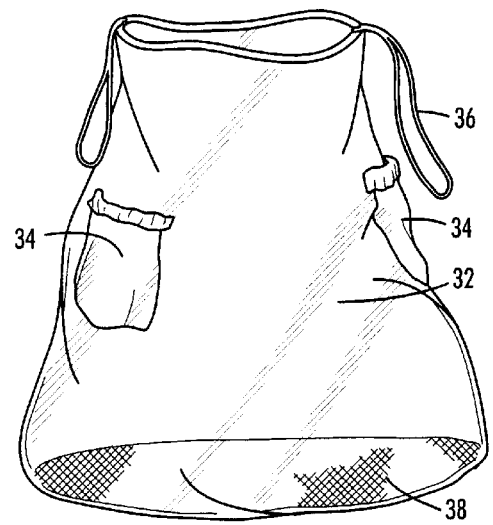
FIG. 5 is a perspective view of the clear storage bag used in conjunction with the baby care protective garment, when the garment is not in use.

A storage bag 32 is also provided, as shown in FIG. 5, to store the protective garment. The storage bag is made from clear thick plastic, or any other suitable material, which is preferably clear. The base 38 of the storage bag is round and flat so that the bag will stand upright, and a drawstring 36 is used around the round opening at the top to secure the contents held therein. A pair of pockets 34 are disposed on the outside of the storage bag for holding baby bottles and the like. The clear material allows the user to view the contents of the bag without having to open the bag.

Figure 6:
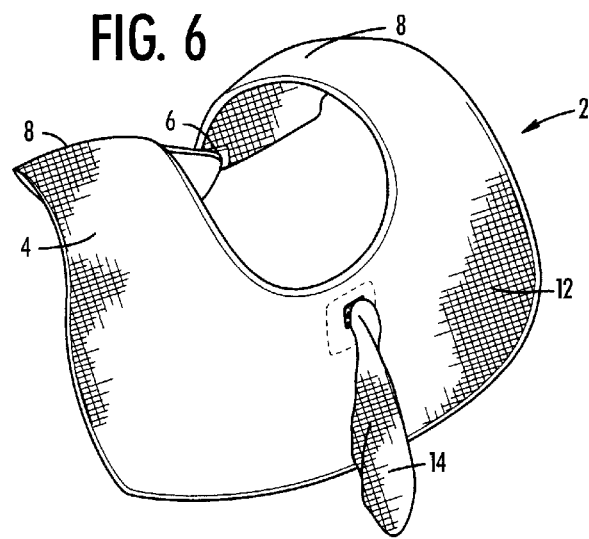
FIG. 6 is a perspective view of an alternate embodiment of the protective garment, showing a smaller version of the garment that covers the shoulders, upper back and upper portion of the torso of a user, and also showing the removable cloth on the front portion and the pocket for the musical device.

FIG. 6 shows another alternate embodiment of the protective garment. In this smaller embodiment, the garment covers the shoulders, upper back, and upper torso of the wearer. The removable cloth is positioned on the front of the garment, and the pocket for housing the musical device is shown on a back side of the garment.

While a preferred embodiment of the invention has been described using specific terms, such description is for illustrative purposes only, and it is to be understood that changes and variations may be made without departing from the spirit or scope of the following claims.

What is claimed is:

1. A machine washable protective garment for use by a person when feeding or burping a baby, and for changing a baby's diapers so that a wearers clothes are protected, said protective garment comprising ,
    a main body member comprising an inner layer made from a waterproof material, and an outer layer attached to at least one side of said inner layer, said outer layer being formed from a soft material suitable for contact with the skin of a baby;
    a cloth member removably attached to said outer layer of said body member for use in wiping food or regurgitated substances from a baby's skin;
    at least one pocket positioned on said outer layer of said body member, for holding a baby bottle, pacifier, or the like;
    an opening through said main body member positioned adjacent a female user's breast, for providing access for a baby to a user's breast for nursing; and
    fastening means for affixing said main body member about a neck of a wearer so that said body member is secured over a user's shoulders and about said user's neck.

2. The protective garment set forth in claim 1, wherein said main body member also includes a small pocket holding a removable musical device so that said musical device within said pocket is readily accessible to a user, but is not accessible to an infant.

3. The protective garment set forth in claim 1, further comprising a lap pad removably positioned on an underside of said main body member so that said lap pad is adjacent a user's body or clothing, wherein said lap pad may be released at a top portion and repositioned on a user's lap for changing a baby's diaper and preventing said user's clothing from becoming soiled, and wherein said lap pad may be resecured to said top portion of said main body member after use.

4. The protective garment set forth in claim 1, wherein said outer layer of said main body member contains shapes or figures that glow in the dark.

5. The protective garment set forth in claim 1, further comprising at least one book and loop fastener style loop attached to said main body member for securing teething rings, pacifiers, baby keys, or the like thereto.

6. The protective garment set forth in claim 1, further including a clear storage bag having a rounded base with clear sides extending upwardly therefrom, and a drawstring disposed about an opening of said bag for securing said opening in a closed position, and further having a pair of pockets disposed on an outer side portion of said bag for holding baby bottles and the like.

7. A machine washable protective garment for use by a person when feeding or burping a baby, and for changing a baby's diapers so that a wearers clothes are protected, said protective garment comprising:
    a main body member comprising an inner layer made from a waterproof material, and an outer layer attached to at least one side of said inner layer, said outer layer being formed from a soft material suitable for contact with the skin of a baby;
    at least one pocket positioned on said outer layer of said body member, for holding a baby bottle, pacifier, or the like;
    fastening means for affixing said main body member about a neck of a wearer so that said body member is secured over a user's shoulders and about said user's neck; and
    a lap pad removably positioned on an underside of said main body member so that said lap pad is adjacent a user's body or clothing, wherein said lap pad may be released at a top portion and repositioned on a user's lap for changing a baby's diaper and preventing said user's clothing from becoming soiled, and wherein said lap pad may be resecured to said top portion of said main body member after use.

8. The protective garment set forth in claim 7, wherein said main body member also includes a small pocket holding a removable musical device.

9. The protective garment set forth in claim 7, wherein said outer layer of said main body member contains shapes or figures that glow in the dark.

10. The protective garment set forth in claim 7, further comprising at least one hook and loop fastener style loop attached to said main body member for securing teething rings, pacifiers, baby keys, or the like thereto.

11. The protective garment set forth in claim 7, wherein said main body member includes an opening positioned adjacent a female user's breast, for providing access for a baby to a user's breast for nursing.

12. A machine washable protective garment for use by a person when feeding or burping a baby so that a wearers clothes are protected, said protective garment comprising:

a main body member comprising an inner layer made from a waterproof material, and an outer layer attached to at least one side of said inner layer, said outer layer being formed from a soft material suitable for contact with the skin of a baby;

a musical device housed within a pocket positioned on an underside of said main body member, so that said musical device within said pocket is readily accessible to a user, but is not accessible to an infant;

fastening means for affixing said main body member about a neck of a wearer so t hat said body member is secured over a user's shoulders and about said user's neck; and a cloth member removably attached to said outer layer of said body member for use in wiping food or regurgitated substances from a baby's skin.

* * * * *